United States Patent [19]

Schenck et al.

[11] Patent Number: 4,553,542
[45] Date of Patent: Nov. 19, 1985

[54] METHODS AND APPARATUS FOR JOINING ANATOMICAL STRUCTURES

[76] Inventors: Robert R. Schenck, 1100 N. Lake Shore Dr., (Apt. 33A), Chicago, Ill. 60611; Harry P. Weinrib, 2644 W. Estes Ave., Chicago, Ill. 60645

[21] Appl. No.: 504,683

[22] Filed: Jun. 15, 1983

Related U.S. Application Data

[63] Continuation-in-part of Ser. No. 548,867, Sep. 29, 1983, , which is a continuation-in-part of Ser. No. 349,885, Feb. 18, 1982, Pat. No. 4,474,181.

[51] Int. Cl.$^4$ ............................................. A61B 17/11
[52] U.S. Cl. ................................................. 128/334 R
[58] Field of Search ............... 128/334 R, 334 C, 335, 128/346, 326, 340

[56] References Cited

U.S. PATENT DOCUMENTS

| | | | |
|---|---|---|---|
| 3,221,746 | 12/1965 | Noble | 128/334 R |
| 3,254,650 | 6/1966 | Collito | 128/334 C |
| 3,254,651 | 6/1966 | Collito | 128/334 C |
| 3,538,917 | 4/1968 | Selker | 128/346 X |
| 4,165,747 | 8/1979 | Bermant | 128/334 C |
| 4,366,819 | 1/1983 | Kaster | 128/334 C |

FOREIGN PATENT DOCUMENTS

| | | | |
|---|---|---|---|
| 395074 | 1/1974 | U.S.S.R. | 128/334 C |

*Primary Examiner*—Michael H. Thaler

*Attorney, Agent, or Firm*—Fitch, Even, Tabin & Flannery

[57] ABSTRACT

The invention provides encircling devices by which anatomical structures, such as blood vessels, fallopian tubes, ureters, vas deferens and outer nerve sheaths are anastomosed. Such an encircling device provides an opening that receives an end of a tubular anatomical structure having a prepared opening, and the tubular structure is anastomosed to a second anatomical structure having a prepared opening by tethering the two structures to the encircling device holding the structures under radial stress in apposition to each other to form a fluid-tight peripheral seal around their openings. Encircling devices are also used to join a tubular anatomical structure to a second anatomical structure having a cavity, e.g., a fallopian tube to a uterus or a uterer to the bladder. The tubular structure is received in the opening of the encircling device and tethered thereto to hold its end open, and then the encircling device is extended through a passageway in the second anatomical structure by means of a trocar, and when the trocar is withdrawn, the large size of the device compared to the passageway, which naturally constricts, prevents the device from removing itself. To hold anatomical structures in close proximity during anastomosis, a pneumatic or hydraulic clamping device is provided which grips the anatomical structures with a precise force according to the fluid pressure supplied thereto. Precise control of gripping force assures a firm grip that is not excessive and does not damage the structures.

13 Claims, 36 Drawing Figures

PATENCY
RING TECHNIQUE VS. CONVENTIONAL

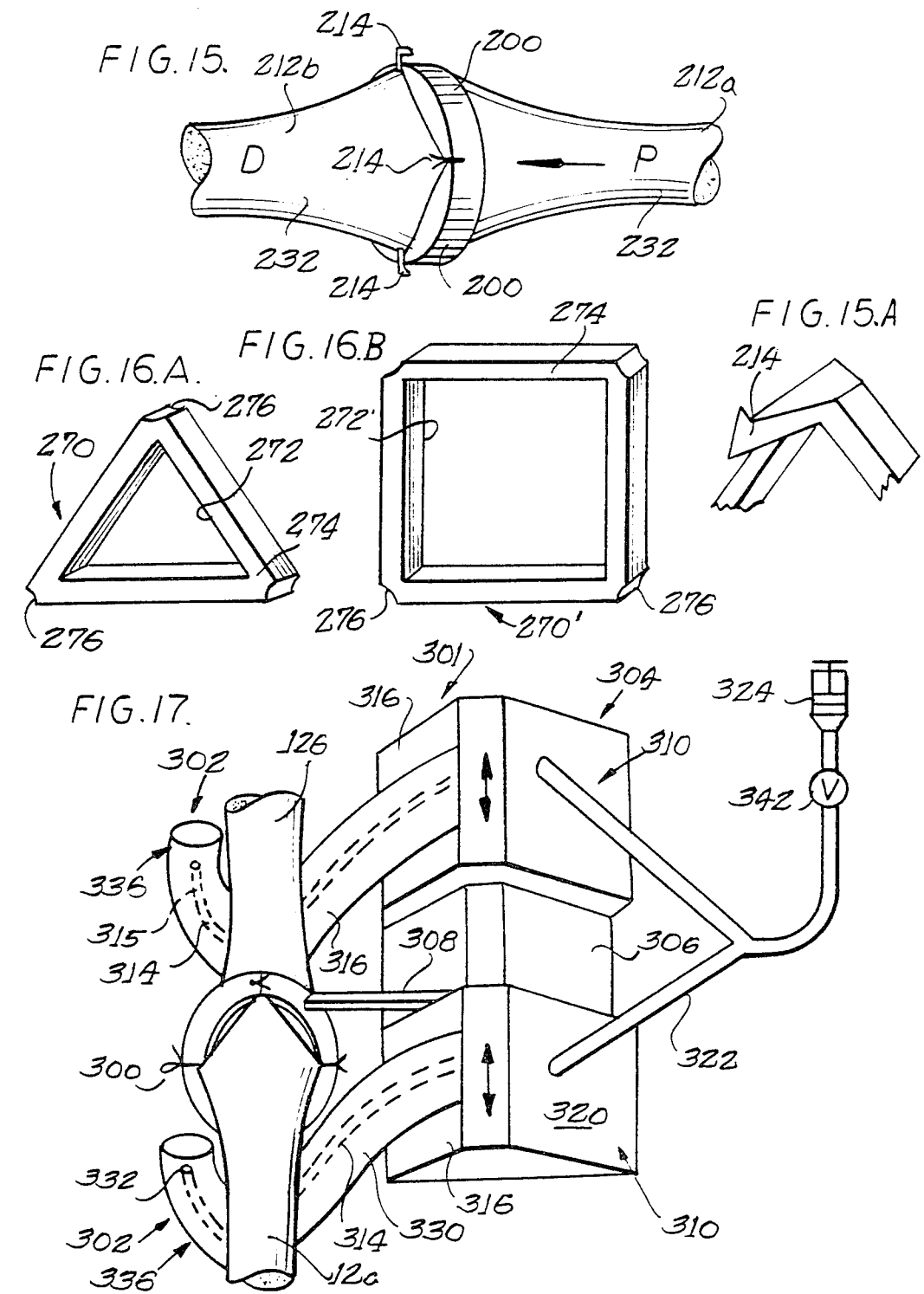

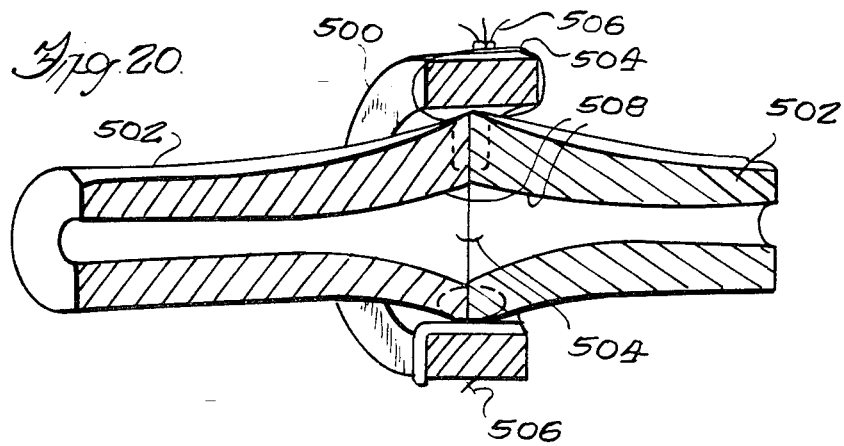
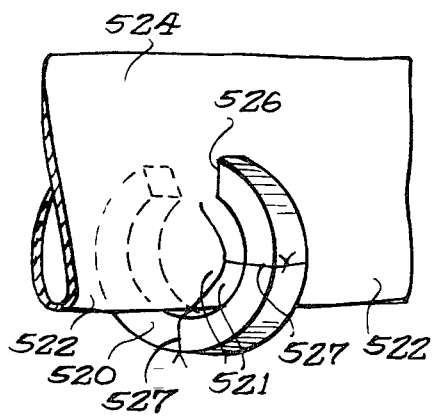
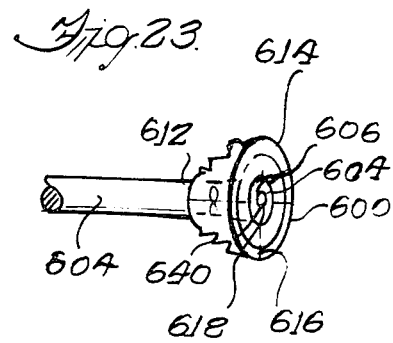
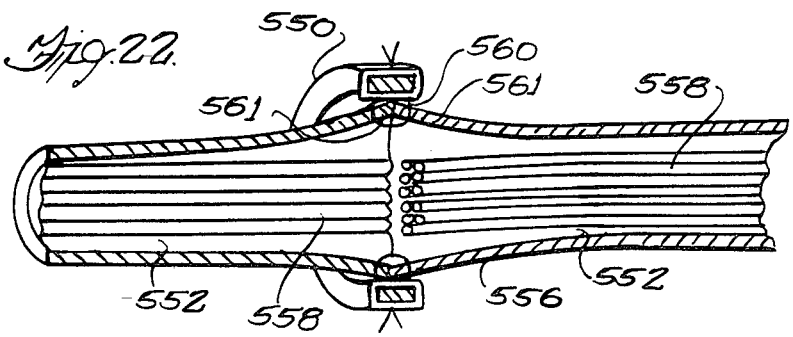

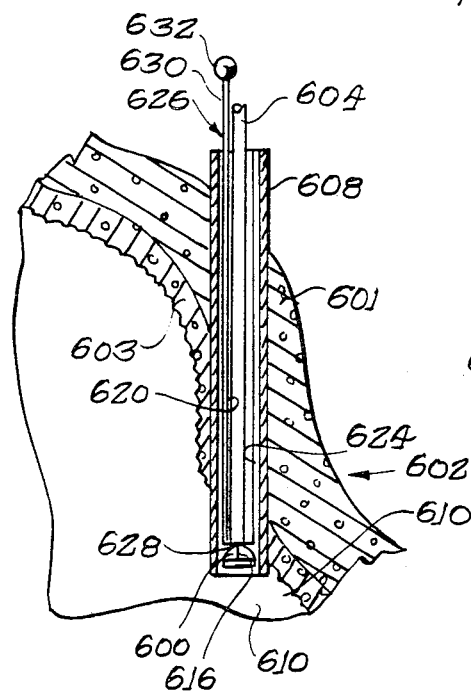
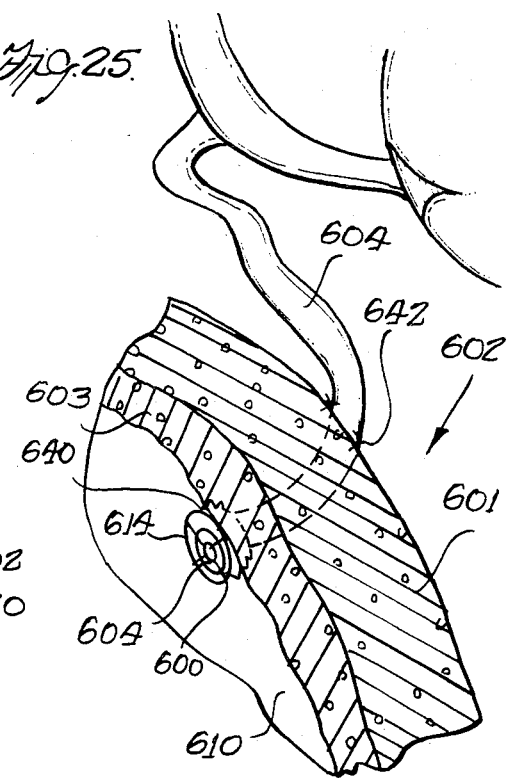
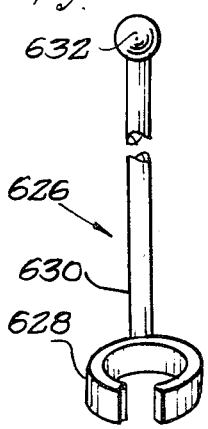
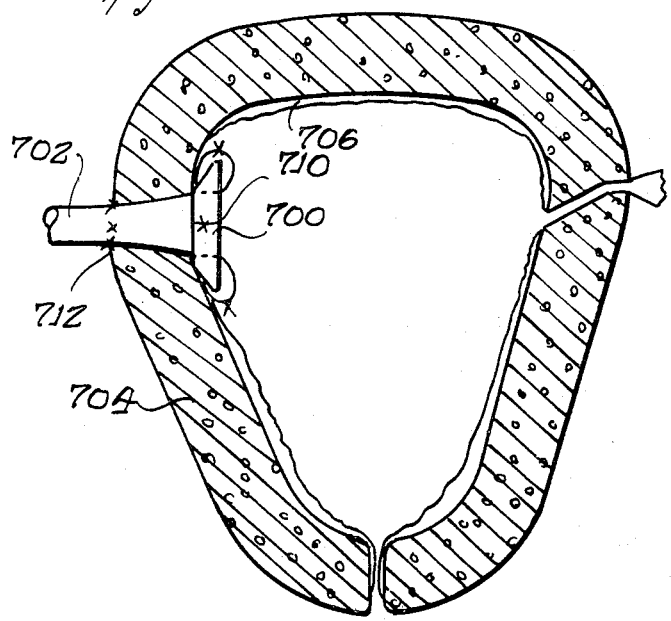

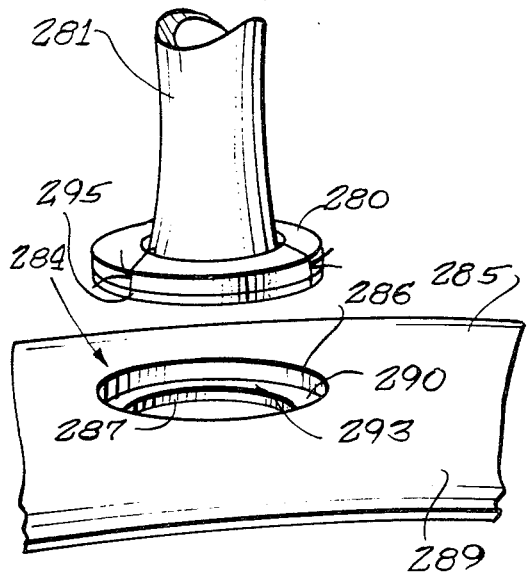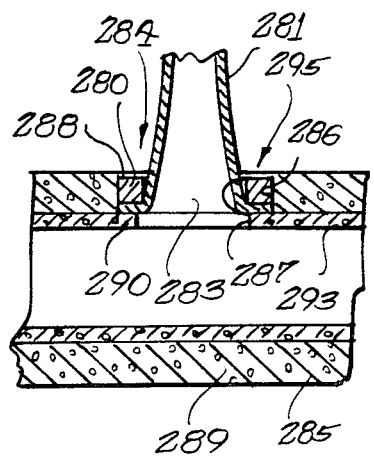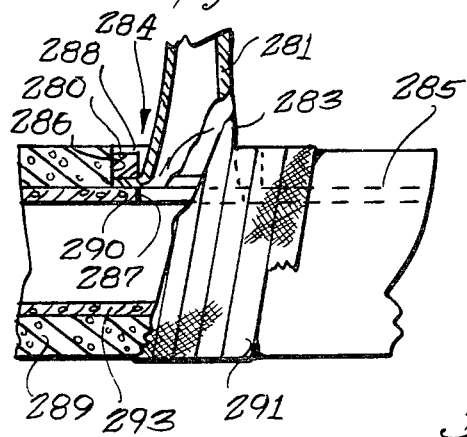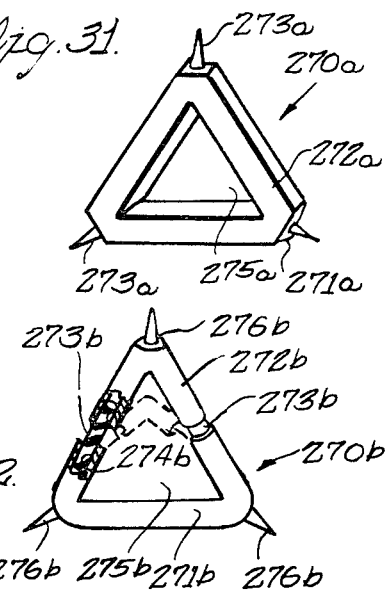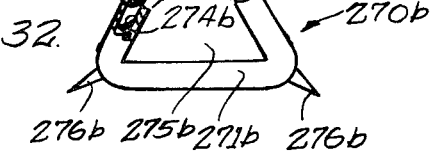

METHODS AND APPARATUS FOR JOINING ANATOMICAL STRUCTURES

This is a continuation-in-part of U.S. patent application Ser. No. 548,867 filed, Sept. 29, 1983, which claims priority from PCT application Ser. No. PCT/US83/00206 filed Feb. 16, 1983 and which is a continuation-in-part of U.S. patent application Ser. No. 349,885 filed Feb. 18, 1982, now U.S. Pat. No. 4,474,181.

The present invention relates to methods and apparatus for joining severed ends of tubular anatomical structures, such as blood vessels.

Among the important and time consuming tasks in surgical procedures is the anastomosis or joining of severed blood vessels, and the success of a surgical procedure may depend on the degree of circulation which is restored through such anastomosis. Anastomosing of blood vessels is a tedious procedure, particularly in blood vessels of small diameter including blood vessels less than one mm. in diameter. Conventional blood vessel suturing techniques are time consuming, extending the duration of a surgical procedure and successful anastomosing of blood vessels is highly dependent on the proper placement of sutures by the surgeon. Particular difficulty is often encountered in anastomosing children's vessels which are small and prone to spasm.

To aid in anastomosing blood vessels, implantable devices which connect severed ends of blood vessels have been described previously, e.g., U.S. Pat. Nos. 3,254,650 and 4,055,186, British patent specification No. 1,181,563, German Fed. Rep. Patent No. 2,101,282 and Nakayama et al. *Surgery* December 1962, pp. 918–931. Devices have also been described for everting severed ends of blood vessels to facilitate their suturing, e.g., U.S. Pat. No. 2,180,337. The need continues for improved methods and apparatus for anastomosing blood vessels, particularly tiny blood vessels.

Blood vessels of all but the largest size, i.e., the aorta and vena cava in humans, have a naturally occuring contractility, identified as circumferential compressive stress, that resists dilation. These forces become proportionately larger as the vessel diameter decreases and the relative wall thickness increases. Radial tethering forces of tissues do exist around the vessel, but these are of lesser significance than longitudinal vessel motion tethering.

Successful suturing of blood vessels does not assure their continued patency, i.e., their ability to conduct blood flow. Thrombosis (clotting of blood) may act to block blood flow through an anastomosed vessel. In addition to inaccurate placement of sutures, several other factors—spasm, stenosis, and microclamp damage—may be additive in causing thrombosis after microvasuclar repair. It has been found that continuity of flow during the first twenty minutes after anastomosis is critical in preventing thrombus formation. It has also been found that platelet aggregation, and later resolution occurs in the first several hours after a microvascular anastomosis.

It is a general object of the present invention to provide methods and apparatus which simplify surgical anastomosis techniques and which effect an anastomosis with substantial assurance of patency.

The problems presented by blood vessel repair are generally common to other tubular anatomical structures, such as the ureter, vas deferens, fallopian tubes and biological sheaths, such as the outer sheath of a nerve bundle.

It is a further general object to provide methods and apparatus which simplify surgical repair of such other tubular body conduits and tubes and to effect their anastomosis with sustained or renewed function.

Herein, an external ring is provided which is placed around one end of a blood vessel portion to be joined. Means, such as sutures or hooks, are provided to radially tether the blood vessel portions to the ring at various circumferal locations to apply outward radial stress to the portions. The tethering holds the intima of the severed ends together forming a fluid-tight seal and promoting healing while minimizing both the number and exposure of the sutures, thereby reducing the likelihood of significant thrombosis occurring at the anostomosis site. The outward radial stress maintains an open blood flow passageway at the junction during healing.

Anastomosis of severed blood vessel portions requires that the severed portions be held in close proximity to permit the surgeon to perform the necessary joining operation. A frequently used type of clamp for this purpose consists of a pair of spring clamps mounted at spaced apart intervals along a bar, each clamp pinching one of the severed blood vessel portions to hold them in place for anastomosis. The force with which the clamps grip the blood vessel must be sufficient to hold them in place, and generally the clamp must exert about 15 gm. pressure. On the other hand, excessive pressure of the metal clamps will damage the blood vessel portions and it is considered very undesirable that a clamp exert over about 35 gm. pressure to the blood vessel. Thus the clamp should grip the blood vessel portions applying pressure within a very narrow range that is difficult to achieve with conventional microclamps.

It is another general object of the invention to provide clamping devices whose gripping force can be precisely adjusted to grip the blood vessel or other tubular anatomical structure with a predetermined amount of force and with less damage to the blood vessel.

The clamping device comes into intimate contact with the internal regions of the body and must be presterilized. During surgery the anastomosis device must be positioned relative to the clamping device. Time could be saved during surgery if the anastomosis device were prepositioned relative to the clamping device.

It is another general object of the invention to provide an anastomosis device which is attached to a clamping device prepositioned therein and easily removable from the clamping device after surgery so that the clamping device can be disposed of.

These and other objectives and advantages of the invention will become more apparent from the following detailed description of the invention in reference to the accompanying drawings in which:

FIG. 15 is a perspective view of the ring of FIG. 13 having two blood vessel end portions tethered thereto;

FIG. 15A is an enlarged perspective view of the hook of the ring of FIG. 16A and 16B.

FIG. 16A is a further alternative embodiment of an anastomosis device having a triangular configuration;

FIG. 16B is a further alternative embodiment of an anastomosis device having a square configuration;

FIG. 17 is a perspective view of an anastomosis ring attached to a pneumatic or hydraulic clamping device embodying various features of the present invention, a pair of blood vessel portions shown clamped thereto;

FIG. 20 is a cross-sectional view of an encircling device, according to the invention, used to anastomose apposed ends of a ureter;

FIG. 21 is a perspective view of an embodiment of an anastomosis device according to the invention having a gap, the device joining severed ends of a fallopian tube and the gap in the device being filled by mesosalpinx tissue;

FIG. 22 is a cross-sectional view of an encircling device, according to the invention, anastomosing apposed ends of a severed nerve;

FIG. 23 is a perspective view of an alternative embodiment of an encircling device used for joining a tubular anatomical structure, such as a ureter, to an anatomical structure, such as a bladder, having a cavity, the encircling device illustrated attached to the tubular anatomical structure;

FIG. 24 is a cross-sectional view illustrating insertion of the encircling device into the cavity of the bladder to extend a ureter through the bladder wall;

FIG. 25 is a cross-sectional view showing the device of FIG. 24 inserted into the bladder;

FIG. 26 is a perspective view of the tool shown in FIG. 24 used to plunge the ring with the tethered ureter into the bladder;

FIG. 27 is an elevation view of an anastomosis device, similar to that shown in FIG. 23, extending a fallopian tube into the uterus, which is shown in cross section;

FIG. 28 is a perspective view of blood vessel portions prepared for an end-to-side anastomosis, including a blood vessel end portion tethered to an encircling device and an atherosclerotic vessel with an opening cored through its side;

FIG. 29 is a cross-sectional view of the blood vessel end portion of FIG. 28 inserted in the side opening cored through the side of the atherosclerotic vessel;

FIG. 30 is a perspective view, partially in section, of the end portion taped into the cored opening of the artheroschleoritic vessel;

FIG. 31 is a perspective view of a further alternative embodiment of an encircling anastomosis device; and FIG. 32 is a perspective view, partially in section, of a further alternative embodiment of an encircling anastomosis device.

Figure 1:
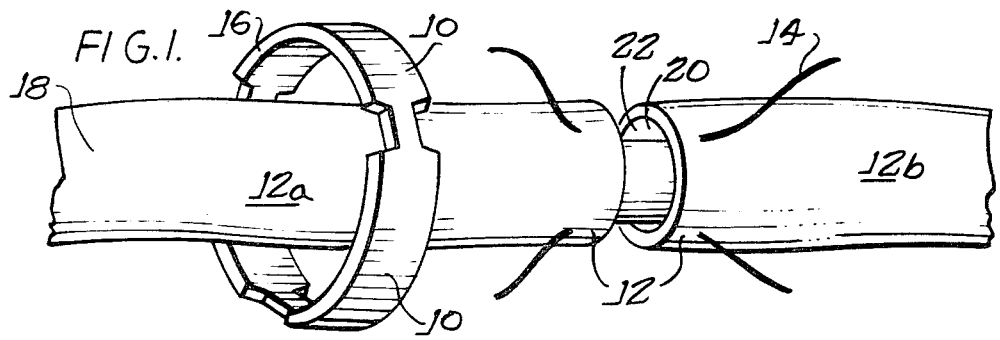
FIG. 1 is a perspective view of an anastomosis ring, embodying various features of the invention, disposed around a severed end of a blood vessel portion and sutures threaded through two blood vessel end portions to be anastomosed.

In accordance with the present invention, severed portions 12 of blood vessels or other tubular anatomical structures are reconnected or an anastomosed with outward radial stress applied to the blood vessel at the anastomosis site to keep blood flow passageways dilated and otherwise maintain patency of the connected blood vessel portions. The portions are anastomosed by placing an external (to the blood vessel) encircling device 10 around an end 12a of one of the severed blood vessel portions 12, tethering the portions 12a,b at three or more locations with means such as sutures 14 or hooks 214 (FIG. 13) to radially outwardly stress the vessel portions everting their intima and holding their intima in fluid-tight apposition. (It is to be understood that the blood vessel portions need not originally be portions of the same blood vessel).

The device 10, illustrated in FIG. 1, is in the form of an annular ring formed of material which is biocompatible for implantation in a living body of an animal, such as a human. The ring 10 has means 19, such as grooves or notches, at spaced-apart locations for tethering sutures 14. The tethering of the connected blood vessel 12 not only holds the blood flow passageway 20 open but dilates the blood vessel portions at the anastomosis site enlarging the blood flow passageway, thereby reducing the chance of thrombosis occurring and clogging the passageway. The stretching also serves to evert the interior surfaces or intima 22 of the blood vessel tightly apposing the intima to aid prompt healing.

The annular shape of the ring 10 corresponds to the generally circular cross section of blood vessels 12. In order to provide for stretching of the connected blood vessel end portions 12l, 12b toward the ring, the interior surface 16 of the ring has an inside diameter at least 25 percent longer than the outside diameter of the blood vessel which the ring is adapted to surround, and preferably the inside diameter of the ring is between 50 percent and 200 percent larger than the diameter of the blood vessel. Although there is no inherent upper limit on ring size as compared to the size of the blood vessel for anastomosis purposes, the ring, being a foreign object within the body, is preferably as small as possible consistent with suture attachment providing radial tethering stress. The ring need be no longer or no thicker than is consistent with its structural integrity.

External anastomosis rings 10 may be formed of any material of sufficient strength to support the tethered blood vessels and is biocompatible or can be made biocompatible with an appropriate coating. Suitable biocompatible materials include but are not limited to stainless steel, graphite, pyrolytic carbon, tungsten, tantalum and polymeric material, such as polytetrafluorethylene. In a preferred embodiment, the ring 10 is formed or a material, which is not only biocompatible but is dissolved or otherwise degraded after a period of time by the body of the animal. Suitable biocompatible materials for rings which are dissolved or degraded after a healing period include collagen, polyglycolic acid, polylactic acid and combinations of polyglycolic, polylactic acid and polyhydroxybutyric acid.

The attachment means 19 provided at spaced-apart locations on the ring 10 facilitate tethering of the sutures 14 to the ring and maintain the positioning of suture ties 26 (FIG. 3) around the ring. At least three such attachment means 19 are provided for tethering the connected blood vessel ends 2a,b at three locations and so insure an open passageway 20 in the connected, tethered blood vessel. The attachment means 19 are preferably evenly spaced, an arrangement which maximizes the passageway size for the number of sutures used, for example, if three attachment means are used, they are disposed about 120° apart around the ring. Increasing the number of attachment means 19, to which are tethered a corresponding number of sutures, tends to enlarge the passageway 20 at the anastomosis site while permitting the use of a smaller tethering ring; however, each additional suture increases the time needed for anastomosis, and accordingly, it is preferred for smaller blood vessels, that only three attachment means 19 be provided for tethering three sutures 14. However, for larger blood vessels, a ring having up to six or more attachment means might be provided.

In the embodiment illustrated in FIG. 1, notches 19 in the ring 10 provide the means for attaching and positioning the sutures 14 during tethering. Three pairs of notches 19 are illustrated, the notches of each pair being formed in opposite ends of the ring 10. Notches 19 are simply formed and conveniently utilized during surgery, requiring no threading or other tedious and time consuming techniques. The surgeon need not tether the sutures 14 initially in the notches 19 but may shift loosely tethered sutures into the notches after the ties 26 have been initially knotted around unnotched portions of the ring 10.

Figure 2:
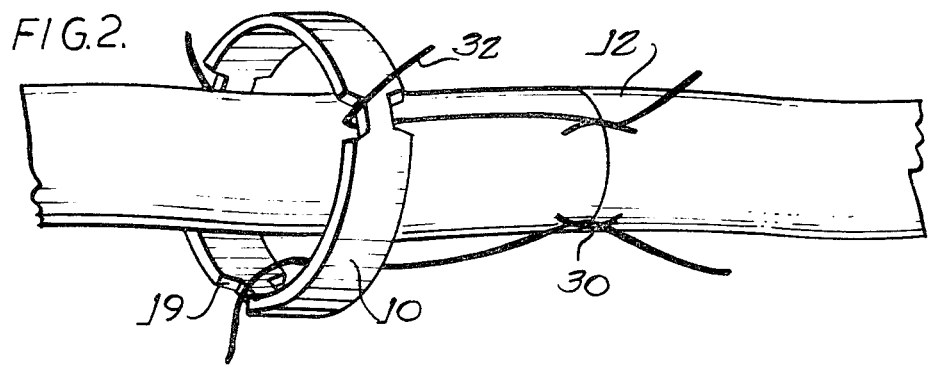
FIG. 2 is a perspective view of an anastomosis ring of FIG. 1 showing the sutures tied to connect the blood vessel end portions by sutures.
Figure 4:
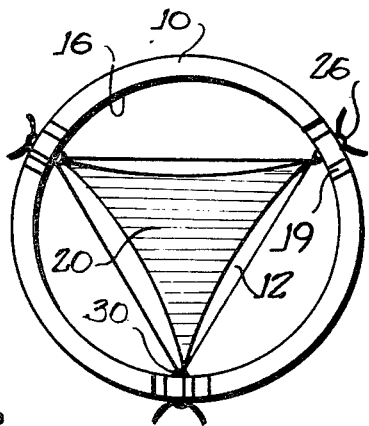
FIG. 4 is a plan view showing one of the two severed ends sutured and tethered to the ring.

To end-to-end anastomose a blood vessel 12, the end portions of the blood vessel are prepared for suturing in a medically acceptable manner, and the ring 10 is placed around one of the severed ends 12a as seen in FIG. 1. The sutures 14, corresponding in number to the notches 19, are then threaded through the walls of the blood vessel portions at spaced apart locations (FIG. 1), each suture being threaded through both of the severed end portions 12a,b in adjacent circumferential locations (FIG. The threaded sutures are then tied into a knot 30 (FIG. 2) connecting the severed end portions 12a,b of the blood vessel and leaving a free end 32 of each suture with sufficient length for tethering to the surrounding ring 10. Thereafter, the free ends 32 of the sutures 14 are looped around the ring 10, drawn outward to pull the blood vessel end portions radially outward toward the ring and tied into knots 26 located within the notches 19. The tethered sutures 14 stretch the blood vessel end portions 12a,b providing a polygonal blood passageway, e.g., where three sutures are used, the passageway is generally triangular as best seen in FIG. 4. Because the walls of the blood vessel portions 12a,b are stretched, the blood vessel end portions are dilated, and the polygonal opening provides a blood flow passageway 20 which is typically as large or larger than the natural circular passageway of the blood vessel.

The stretching of the blood vessel portions by the tethering sutures 14 also everts the intima 22 of the blood vessel end portions 12a, 12b and hold them in tight apposition to each other, as seen in FIG. 4, so that a fluid-tight seal is formed therebetween, and flowing blood primarily contacts the intima of the connected blood vessel end portions. Fewer sutures 14 are used than are generally used in conventional anastomosis techniques, and the tenting effect achieved by tethering minimizes the exposure of the sutures 14 to flowing blood, thereby reducing suture-induced thrombosis.

Figure 7:
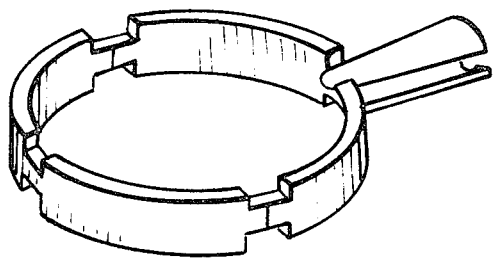
FIG. 7 is a perspective view of an alternative embodiment of an anastomosis ring having means for tethering four blood vessel-connecting sutures.
Figure 8:
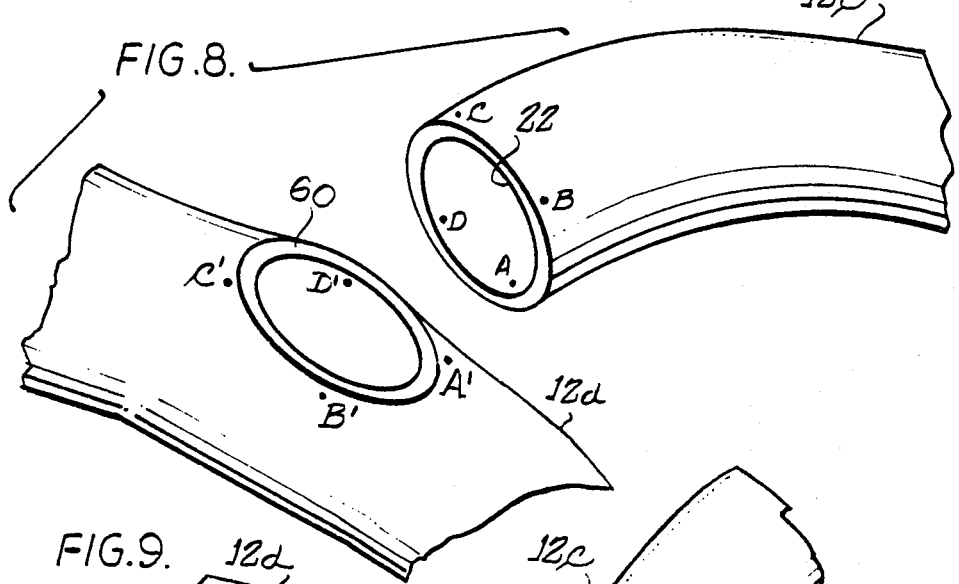
FIG. 8 is a perspective view of an end of one blood vessel prepared for anastomosis to a prepared side of another blood vessel.
Figure 9:
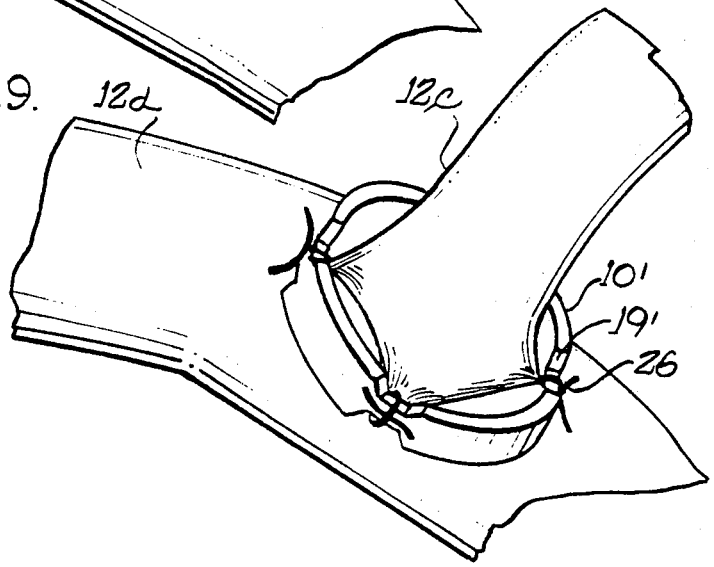
FIG. 9 is a perspective view of the end-to-side anastomosis performed with the ring of FIG. 7 on the prepared blood vessel of FIG. 8.

Illustrated in FIGS. 7–9 is an end-to-side anastomosis, such as may be used to form a shunt between one blood vessel portion and another. The illustrated anastomosis uses an anastomosis ring 10' having four notch pairs 19' spaced 90° from each other for attaching four tethering sutures 14. In this case, a prepared end portion 12c of one blood vessel is connected to another blood vessel portion 12d which has been prepared for anastomosis by cutting a generally circular opening 60, substantially the same size as the passageway 22, through side wall of the blood vessel end portion 12c. The interior diameter of the ring 10' is significantly larger than the exterior diameter of the blood vessel end portion 12c so that when the blood vessel portions 12c,d are joined, the ring is spaced radially outward from the anastomosis site, whereby the tethering sutures 14 apply outward radial stress to the connected portions.

Four discontinuous sutures are used to connect the prepared portions 12c,d (FIG. 8) by threading them through locations, indicated at A, B, C, and D, generally evenly spaced around the circumference of the end portion 12c and corresponding locations A', B', C', and D', generally evenly spaced around the opening 60. The sutures 14 are tied to connect the vessel portions 12c,d and then tethered to the four pairs of notches 19' to form the generally square anastomosis illustrated in FIG. 9.

Figure 11:
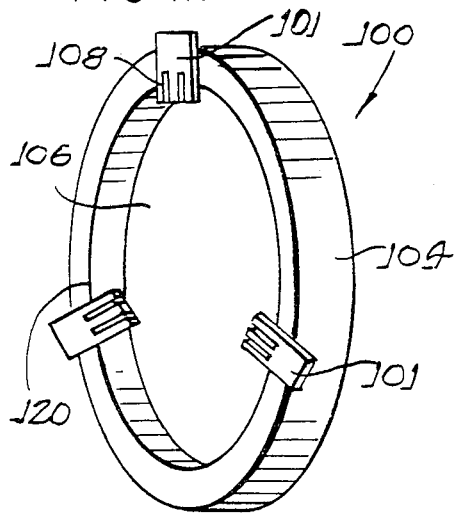
FIG. 11 is a perspective view of a further alternative embodiment of an anastomosis ring having preattached sutures and surgical needles.
Figure 11A:
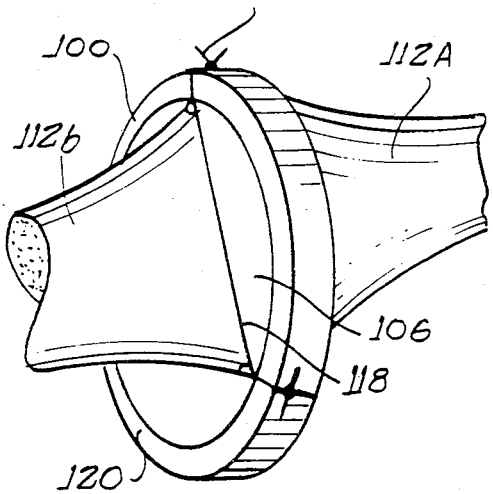
FIG. 11A is a perspective view of the anastomosis ring of FIG. 11 with a pair of blood vessel portions sutured thereto.
Figure 12:
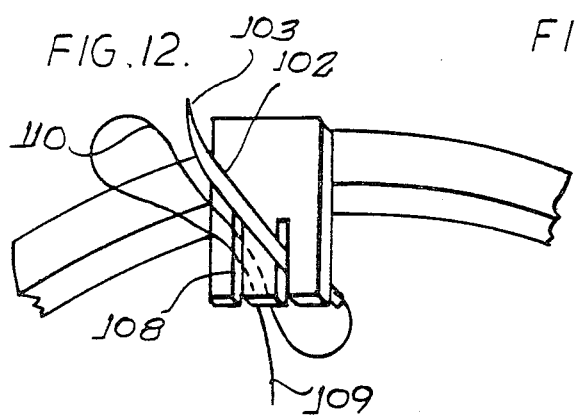
FIG. 12 is a perspective view of the suture and surgical needles of FIG. 11.

Further convenience for the surgeon permitting faster surgery is provided by pre-attaching sutures 101 and needles 102 to an anastomosis ring 100 as illustrated in the embodiment shown in FIG. 11. The ring 100 is a section of a tube formed of a bioabsorbable or biodegradable material, such as polyglycolic acid, has an exterior surface 104 and an interior opening 106. The exterior and interior surfaces may be circular, as in FIG. 11, or they may be triangular, as shown in FIG. 16A, or they may be rectangular or square as shown in FIG. 16B. At the corners of the interior opening 106, a suture holder 101 is fastened with an adherent. The holder is a small sheet of paper or light plastic with two slits 108 to keep needles 102 (FIG. 12) with a preformed loop of suture 110. Needles 102 will be used just for one stitch and disposed so it can be made from the hard plastic or steel. When the needle end 103 has been inserted and passed through the two vessel walls, it is then projected into and passed through the preformed loop 110, and when traction on the needle end and the tail 109 is given, a knot is automatically formed under the ring. The two ends are then tied around the ring in the usual fashion.

The ring 100 with four threaded sutures is packaged as a unit in a sterile manner. During surgery, the physician merely had to place the ring 100 around one severed blood vessel end portion 112*a* and then pierce each needle end 103 through adjacent locations of two blood vessel portions 112*a*, 112*b*, extend each needle through the suture loop 110 and tie a surgical knot using the preformed loop. After the knot 114 is tied, the free ends of the suture 101 are cut to remove the needles 102, which are disposed of, and the holders 101 also may be detached and disposed of.

Three or four knots are used to tether the joined blood vessel portions 112 under radial tension to the corners of the square or triangular interior opening 106 holding the intima of the blood vessel portions 112 in fluid tight apposition to each other. Between the corners of the opening 106, the edges 118 of the dilated, joined blood vessel portions 112 are stretched to extend closely adjacent the side edges 120 whereby the ring 100 and blood vessel portions mutually support each other in axial alignment helping to maintain patency of the blood vessel during healing.

Figure 13:
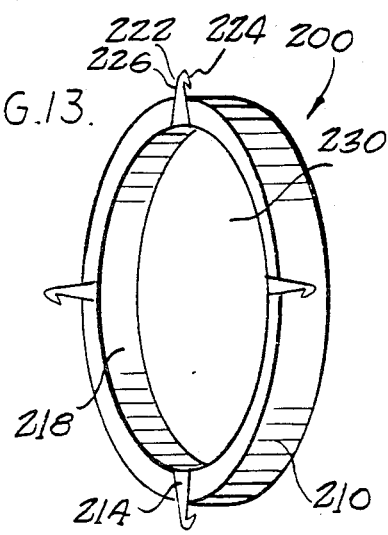
FIG. 13 is a perspective view of a still further embodiment of an anastomosis ring.
Figure 14:
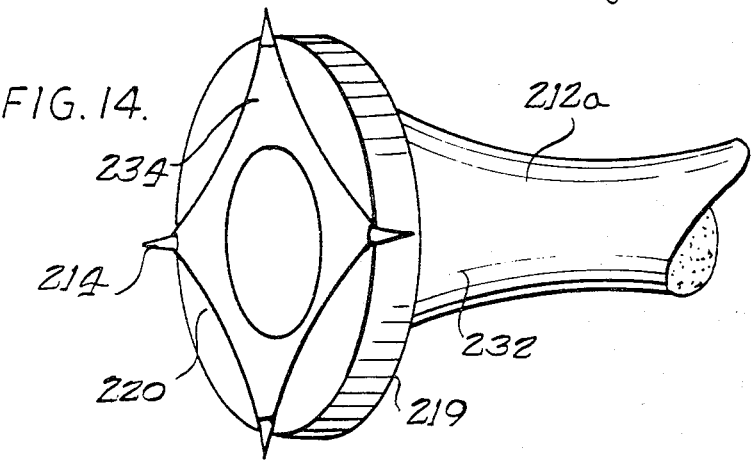
FIG. 14 is a perspective view of the anastomosis ring of FIG. 13 having one blood vessel end portion tethered thereto.

Illustrated in FIGS. 13–15 is an embodiment of a ring 200 in which severed blood vessel portions 212*a*, 212*b* are intimately apposed through radial tethering without the use of sutures. Instead, the blood vessel portions are tethered to the ring 200 by means of hooks 214 integrally formed with the ring and disposed at evenly spaced locations at points along a circle of greater diameter than the diameter of the blood vessel portions 212. The illustrated ring 200 has a circular exterior 210, a circular interior 218 and flat end faces 219, 220. The hooks 214 are formed as protuberances raised from one end face 220 and have portions 222 that extend outward beyond the ring exterior 216. Each outwardly extending portion 222 has a doubled backed segment 224 with a pointed end 226 for puncturing the blood vessel portions 212. Doubling the end segment 224 back so that the point 226 extends inward toward the body of the ring 200 forms a fish hook to hold the blood vessel portions against removal and minimizes irritation of the hooks 214 to surrounding tissue.

Because the hooks 214 are integrally formed with the ring 200, the ring cannot be fomed merely by segmenting a tubular piece of ring material, and manufacture of the hooked ring is somewhat more difficult than manufacture of the ring embodiments described above. A ring 200 having integrally formed hooks 214 may be formed by molding a bioabsorbable or biodegradable material, such as polyglycolic acid. To prevent the ring material from sticking in the mold, a release agent is used to coat the mold. The release agent is selected for biocompatibility so that any release agent adhering to the ring will not induce adverse reactions.

The sutureless tethering ring 200 is disposed around one severed blood vessel end portion 212*a* with its hooked face 220 outward relative to the blood vessel end portion 212*a* as seen in FIG. 14 so that the blood vessel end portion extends entirely through its central opening 230. With forceps, the surgeon drapes a portion of the severed blood vessel end portion 212*a* over one hook 214 so that the hook punctures the blood vessel wall from its exterior 232 to its intima 234. The surgeon then repeats the procedure hooking the blood vessel portion 212*a* at evenly spaced locations until the blood vessel portion 212*a* is tethered under tension over the hooked face 220 of the ring 200 exposing a broad region of its intima 234. Next, the surgeon grasps a portion of the end of another severed blood vessel portion 212*b* and draws it over one hook 214 so that the hook punctures the blood vessel portion from its intima to its exterior 232. The procedure is repeated hooking the other blood vessel portion 212*b* at evenly spaced locations, tethering the blood vessel portion under tensions to the hooks 214 and bringing a broad portion of the intima of the blood vessel portion 212*b* into apposed contact with the intima 234 of the blood vessel end portion 212*a* that was initially tethered to the ring 200, thereby completing the anastomosis. Similar hooks can also be placed in the triangular and quadrangular configurations shown in FIGS. 16A and 16B. These are shown in FIG. 15A.

Illustrated in FIGS. 16A and 16B are alternative embodiments of anastomosis devices, 270, 270′ which instead of being ring shaped are configured as polygons with polygonal shaped central openings 272, 272′. The number of verticies 274′ of the polygon correspond directly to the number of sutures that are to be used for tethering the connected blood vessel portions, and the sutures are tethered to the verticies of the polygon which represent the points most remote from the geometric center. Thus the embodiment of an anastomosis device 270 shown in FIG. 16A is configured as an isosceles triangle and is used for anastomosing blood vessel portions with three sutures while the device 270′ in FIG. 16B is square and is used for anastomosing blood vessel portions with four sutures.

As a means for attaching the sutures, the vertices are machined to provide concave grooves 276 facing outward. Under certain circumstances, it is found that such grooves 276 provide better resistance to suture slipping during surgery than do notches at the ends of rings. Like in the circular embodiments, the locations where the sutures are attached lie along a circle of substantially greater radius than the unstretched radii of the openings of the blood vessel end portions.

An advantage of polygonal shaped devices 270, 270′ over a ring shaped device is that the polygonal central openings of the devices correspond to the shape that the blood vessel ends assume when they are tethered under radial stress allowing an anastomosis device of minimum size to be used. A polygonal anastomosis device is selected according to the radii of the openings so that when stretched, the end edges of the tethered vessel portions extend to the sides of the polygonal shaped interior opening 272 and 272′.

Although square and triangular devices 270, 270′ are shown for tying three and four sutures respectively, polygonal devices having more vertices 274 for attaching additional sutures can be formed. However, the size advantage relative to a circular configuration diminishes as the number of vertices increase. Also these shaped devices can be used for the sutureless technique by adding thereto the additional hooks 214 as shown in FIG. 15A.

Illustrated in FIG. 31 is a triangular anastomosis device 270*a* adapted for sutureless tethering. Flattened outer surfaces 271*a* are provided at each of the verticies 272*a*, and conical protrusions 273*a* extend radially outward from the flattened surfaces. One end of a blood vessel or similar tubular anatomical structure is inserted through the opening 275a of the encircling device 270a, and the prepared blood vessel end stretched over and impaled on each of the three conical protrusions. Then the second prepared blood vessel end is impaled on the conical protrusions, apposing the intima of the blood vessel end portions. A particular advantage of the sutureless anastomosis device having the radially extending protrusions is its simplicity, making it expecially suitable for formation by molding.

Illustrated in FIG. 32 is an anastomosis device 270b which is similar to the device 270a illustrated in FIG. 31 except that the device is formed in two body portions 271a, 272b and joined together by short flexible segments 273b which permit the anastomosis device to be deformed out of plane (as shown in ghost in FIG. 32) to facilitate its insertion into the lumen of prepared blood vessel ends. The larger "U-shaped" body portion 271b and smaller "V-shaped" body portions 272b are molded from relatively rigid biocompatible, bioabsorbable material, such as collagen, or polyglycolic acid. Blind bores 274b are formed in the adjacent ends, and the ends are connected by the short tubular segments 273b received in an interferrence fit in the blind bores. The tubular segments are formed of resilient, flexible material, such as bioabsorbable, multifilament suture. A suitable flexible suture material is multifilament polyglycolic acid, sold under the trade name Dexon. The length (X) of the tubular segments between the body portions is generally between about one tenth and about one fourth the distance between the verticies, i.e., the tethering locations.

The deformability of the device 270b provided by the flexible tubular segments 273b facilitates tethering of the blood vessel ends thereto. The first prepared end is inserted through the opening 275b and everted around the device and impaled on at least one conical protrusion 276b. Thereafter, the device 270b is deformed out of plane making it easier to insert the remaining protrusion into the everted blood vessel. The resilient tubular segments 273b have a "memory" that causes them to return to their straight-line configuration and return the device to its planar configuration, and as it returns to its planar configuration it stretches the prepared end of the blood vessel. The second prepared blood vessel end is then joined to the device, initially by penetrating the blood vessel end at one point with one of the protrusions 276b and then again deforming the device and inserting the device into the lumen so that the remaining protrusions penetrate the blood vessel end. When the device springs back from its deformed configuration into its planar configuration, the intima are held apposed and the lumen at the junction held open wide.

The invention also contemplates a unitary anastomosis device which is deformable out of plane. Providing such a unitary device requires a material which is sufficiently flexible to be deformed by the surgeon but which springs back into its non-deformed state, tethering the blood vessel end portions until the opposed blood vessel end portions until the heal.

A specialized use of an encircling anastomosis device 280 according to the invention relates to end-to-side anastomosis of blood vessels with atherosclerotic disease in which a substantial amount of plaque has built up along the interior surface of the vessel constricting its lumen. Atherosclerotic vessels are hardened and difficult to suture. If a patient (typically an older patient) suffering from atherosclerotic disease sustains extensive damage to his vascular system, the vascular system will often have to be reconstructed using vessel-containing tissue from other parts of his body. The vessels in the legs are the most susceptable to atherosclerotic disease, and when repair of leg damage requires a free flap of tissue obtained from elsewhere on the body, the surgeon may be presented with the need to perform anastomosis on several atherosclerotic vessels.

A method of anastomosing a free end of a blood vessel 281 to the side of an atherosclerotic vessel 285 is illustrated in FIGS. 28-30. A blood vessel end portion 281, which may be obtained from a free flap of tissue, is tethered to the anastomosis device 280 by three or four sutures 295 radially stressing the vessel at its prepared opening to bring the vessel into contact with the ring and expand its lumen 283.

An opening 284 is cored through the side of the atherosclerotic vessel 285 with a special coring instrument which forms an opening portion 286 through the blood vessel wall 289 that is matched in diameter to the exterior diameter of the encircling device and forms a smaller coaxial opening portion 287 through the atherosclerotic plaque 293 itself.

As seen in FIG. 28, the device 280 with the tethered end of the vessel 281 is then placed in the larger diameter opening portion 286 with the intima of the vessel end 281 in contact with an annulus 290 of plaque 293 that is left by the coring operation. Preferably the device 280 has a thickness no greater than the thickness of the wall of the atherosclerotic blood vessel 285 (exclusive of the plaque) so that the top surface 288 of the device 280 locates even with or below the outer surface of the blood vessel.

If the disease has not progressed so far that the natural wall 289 of the vessel has become too hard to suture, the device 280 with the tethered end of the blood vessel 281 may then be sutured to the vessel wall. Alternatively, a biocompatible adhesive tape 291 is wrapped around the blood vessels 281, 285 to hold the device 280 within the opening 284 as shown in FIG. 30.

In accordance with another aspect of the invention, an anastomosis ring 300 is prepositioned within a clamping device 301 such as that shown in FIG. 17, which holds the severed blood vessel portions 12a, 12b in close proximity to each other. The clamping device 301 provides a pair of clamps 302, one for holding each of the blood vessel portions 12a, 12b to be joined and base assembly 304 which carries the clamps 302 spaced apart a predetermined longitudinal distance 300. The anastomosis ring 300 is preferably integrally formed with a member or bar 306 of the base assembly 304, connected thereto by a frangible web 308 allowing the ring 300 to be easily detached from the base bar 306 after anastomosis.

In accordance with a still further aspect of the invention, the clamping device, indicated generally at 301, for use with an anastomosis ring 300 has clamps 302 which are pneumatically actuated to grip the blood vessel portions 12a, 12b with a force that is a function of fluid or air pressure supplied to the clamps 302.

In the embodiment of the ring 300 and attached clamping device 301 illustrated in FIG. 16, a base bar 306 is generally in the shape of a triangular prism, and the anastomosis ring 300 is similar to the ring shown in FIG. 13 or in FIGS. 16A, or 16B. The base bar 306 and ring 300 as well as the frangible connecting web 308 extending between the base bar and the ring are integrally formed of bioabsorbable or biodegradable material, although only the ring is intended to be implanted in the body. The relative simplicity of the base bar 306 and ring 300 permit them to be formed by molding followed by some minor machining of the molded device.

As a means to adjust the axial or longitudinal spacing between the clamps 302 according to surgical requirements, the clamps are not directly joined to the base member but are carried by a pair of end caps or housings 310 which are interfitted to the base bar 306 and are slidable relative thereto. Thus, each housing 310 may be slid along the stationary bar 306 to adjust the spacing between housings.

The pneumatically or hydraulically operated clamps 302, which each extend from a front wall 316 of the end caps 310, are in this instance of the illustrated embodiment of the invention generally U-shaped in order to hold or grip the blood vessel portions 12a and 12b. The shape of each clamp 302 is defined by a rigid hollow tube 314 with a U-shaped cradle portion 315 extending from the front wall 316 of the end cap 310. The hollow tube 314 extends through the end cap 310 above the base bar 306, and a portion 320 extends outward from the rear wall 314 of the end cap 310 providing a port means for connection to flexible tubing 322 through which a pressurized fluid, such as air, is introduced from a source 324. Extending forward of the end cap 310 surrounding the cradle portion 315 of each hollow tube 314 is an elongated inflatable hollow, flexible tube or bladder 330 to which fluid is introduced via an open end 332 of the hollow tube 314. The degree of inflation of each bladder 330 determines the size of the cradle 336 and thereby the force of the clamp 302 on the blood vessel portion 12. By connecting flexible tubing 322 from the rearward portion 320 of the hollow tube 314 to a conduit 322 from the pressurized fluid source 324 having a control valve 342, the gripping force of the clamp 302 is very precisely predetermined and typically adjusted to provide between about 15 and about 25 gm. of force. With such precise adjustment, a firm grip can be assured without danger of microclamp damage to the blood vessel portions.

During surgery, the blood vessel portions 12a, 12b to be joined are loosely positioned in the cradles 336 of the clamps 302 providing sufficient blood vessel lengths inward of the clamps to bring their ends into close proximity. Then the bladders 330 are inflated by opening the valve 342 from the pressurized fluid source 324 to the degree necessary to provide the pressure corresponding to the desired gripping force of the clamps. With the blood vessel portions 12a,b clamped and the anastomosis ring 300 positioned in axial alignment with the clamp cradles 336, anastomosis is effected as described above, and upon completion, the bladders 330 are depressurized releasing the grip of the clamps from the anastomosed blood vessel. The web 308 is broken, and the clamping device 301 is removed.

The clamping device 301 is prepackaged with the attached ring 300 in a sterile manner, and upon opening the package (not shown), the device is immediately ready for use except perhaps for a quickly effected clamp spacing adjustment. The simple design of the clamping device 301 allows it to be manufactured relatively cheaply, an important consideration as it is intended that the entire clamping device be disposed subsequent to use.

Figure 18:
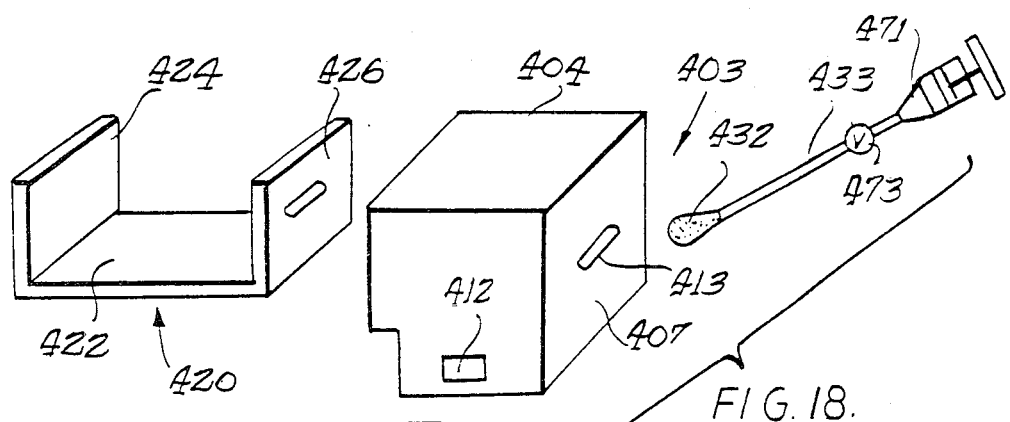
FIG. 18 is an exploded perspective view of parts of an alternative embodiment of a pneumatic or hydraulic clamping device shown in FIG. 19.
Figure 18A:
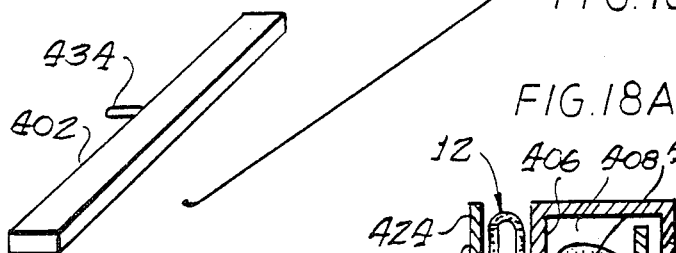
FIG. 18A is a reduced size cross-sectional view taken through the device of FIG. 19.
Figure 19:
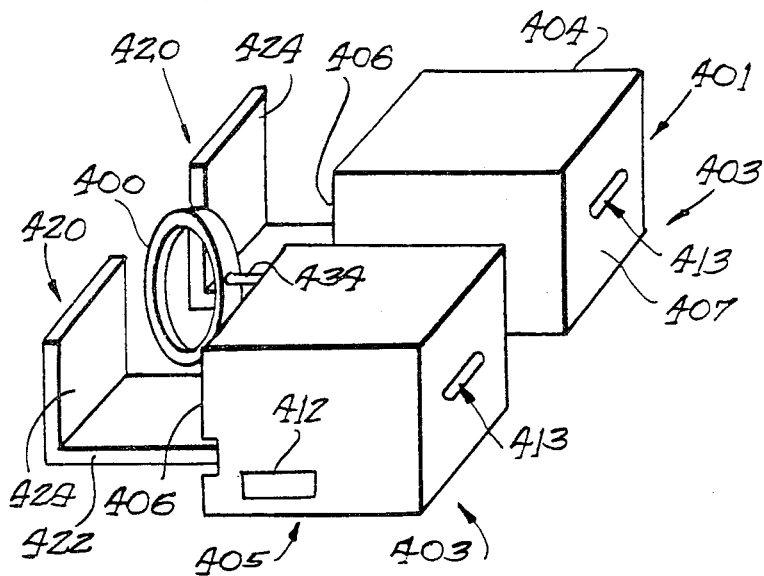
FIG. 19 is a perspective view of a pneumatic or hydraulic clamping device.

Illustrated in FIGS. 18 and 19 is another embodiment of a pneumatically or hydraulically actuated clamping device, indicated generally at 401, which provides for precise determination of clamping force and which may be preattached for sterile packaging to an anastomosis ring 400. A base bar 402 is shaped as a rectangular bar on which is slidably mounted a pair of box-like hollow housings or chambers 403 each having a top 404, bottom 405, front 406, back 407 and a hollow rectangular interior region 408. Within the interior region 408 a pair of clamps 420 is placed. The base bar 402 is sized to fit snugly and intimately in slots 412 in the housing 403 and friction will hold the housing in adjusted positions on the base bar.

The slidable clamps 420 each include a bottom segment 422, an upwardly extending front flange 424, and an upwardly extending rear flange 426. The clamps 420 are interfitted to the chambers 403 with their bottom flanges 422 located over the base bar 402 with the rear flange 426 fully within the interior region 408. A blood vessel holding cradle 431 is defined between the chamber's front wall 406 and the front flange 424 of each clamp 420.

As a means to slide the clamps 420 rearward within the chamber 403, an elongated inflatable tube or bladder 432 is placed between the front wall 406 of the housing 403 and the upward rear flange 426. When pressurized with fluid or air, the bladder expands in size and acts to move the upward rear flange 426 and sliding the clamps 420 rearward and reducing the distance between the front side wall 406 of the chambers and the front cradle flange 424. The bladder 432 is pressurized from a source 471 through a conduit 433 extending through an aperture 413 in the rear wall 407 and rear flange 426 of the clamps 420. A valve 473 in the fluid or air conduit 433 is adjustable to inflate bladder 432 to the degree necessary to obtain the desired clamping force.

The anastomosis ring 400 extends forwardly from the base bar 402 and is connected thereto by a frangible web 434 which holds the prepositioned ring 400 in alignment with the vessels being clamped or gripped in the respective cradles.

Clamping is preformed by positioning the blood vessel 12, in the cradles and pressurizing the bladder 432 to effect clamping. The clamped vessel positions 12 are anastomosed by use of the prepositioned ring 400, and then the clamping pressure is released and the frangible web 434 broken to release the anastomosed blood vessel. After surgery this simplistic clamping device can be disposed.

The clamping or gripping members are preferably formed of soft plastic which provides a softer and more forgiving clamping or gripping pressure than the metal clamps heretofore used. With the pneumatic graduated pressure and these softer materials the pressure and force application to the blood vessels are such as should reduce damage to the latter.

The use of pneumatically or hydraulically actuated and adjustable clamping devices, as described with reference to the above embodiments, permits microsurgery with substantially no microclamp damage to blood vessels, vas deferens, fallopian tubes, or ureter. Prepositioning of the anastomosis device within the clamping device can be expected to significantly shorten surgery, particularly where a large number of blood vessels need to be joined.

The anastomosis devices and their surgical uses will now be described in greater detail by way of specific example.

EXAMPLE I

Conventional and external ring technique anastomoses were performed on the superficial epigastric arteries on alternate sides of each of thirty male Sprague-Dawley strain rats weighing between 200 and 250 grams. Group 1 consisted of twenty external ring technique and twenty conventional technique anastomoses that were explored at one week, and again at four to six weeks. Group 2 consisted of ten external ring technique and ten conventional technique anastomoses that were left undisturbed until exploration at six weeks.

The rats were anesthetized with intraperitoneal pentobarbital, and the superficial epigastric artery was exposed through a transverse inguinal incision. External vessel diameters were 0.3 to 0.5 mm., measured prior to arterial isolation to avoid diameter variation induced by spasm or dilation due to smooth muscle relaxation by topical lidocaine. It was observed that an artery measuring 0.4 mm. in its undisturbed state could vary from 0.2 to 0.6 mm., from maximum vasoconstriction to maximum relaxation.

Three sutures 14 were used for the external ring technique, four to six sutures were used for the conventional anastomoses, dependent upon vessel diameter. Monofilament 100 nylon (Ethilon, Ethicon, tapir point BV75 needle) was used for all anastomoses, and the operations were performed at $25 \times$ to $50 \times$ magnification. The pattern of arterial pulsation was observed, and a radical patency test was performed thirty minutes after completion of each anastomosis to confirm initial patency.

Figure 3:
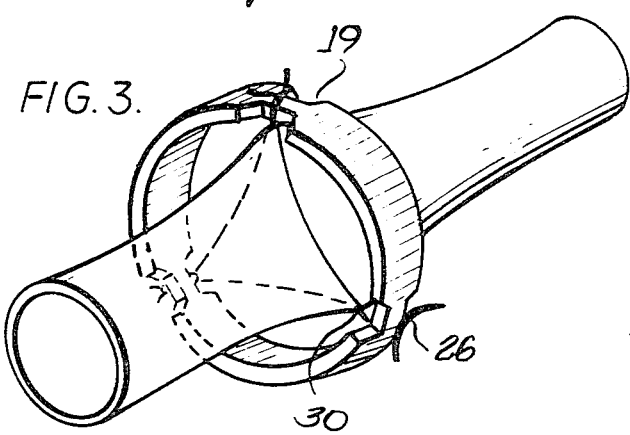
FIG. 3 is a perspective view of the ring of FIG. 1 with the sutures tethered to the ring.

The anastomosis rings 10 comprised 0.2-0.3 mm lengths of 18 gauge polytetrafluoroethylene tubing having pairs of trapezoidal notches 19 formed at three locations 120° apart. For the external ring technique, the blood vessel 12 was placed in an adjustable double microclamp and transected. The loose adventitia was resected and the vessel ends irrigated with heparinized saline solution. Prevention of spasm was aided by the external application of 1% lidocaine. The ring 10 was slipped over one vessel end 12a, and three interrupted sutures 14 were placed through the full thickness of the vessel wall at 120° intervals, leaving the suture ends 32 untied. The vessel ends 12a,b were approximated by tying a surgeon's knot 20, and a free end 32 of all three sutures 14 were passed underneath the ring (FIG. 3). The ring 10 was centered over the anastomosis site, and each of the sutures 14 were tied around the ring 10 at the location of the preformed notches 19 (FIG. 4). In cross section, the vessel 12 then assumed a triangular pattern at the anastomosis site, with the natural elastic forces aiding tight apposition of the edges of the vessel intima between the three sutures 14. Distal release of the double microvascular clamp allowed retrograde flow, followed by proximal release and restoration of antero- grade pulsatile flow.

Figure 5:
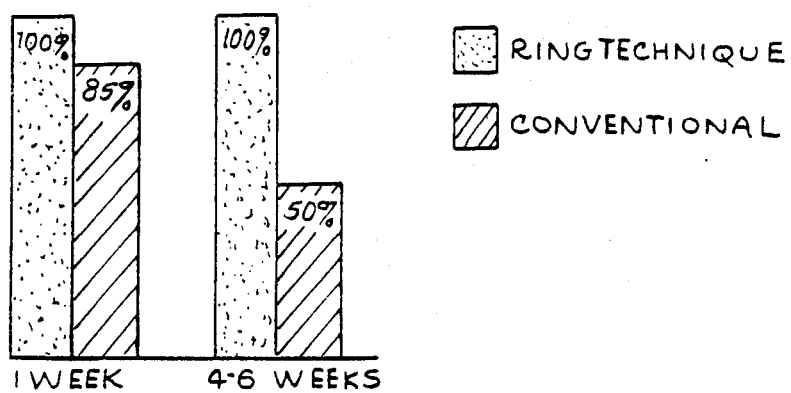
FIG. 5 is a bar graph representing patency of rat blood vessels sutured using the ring of the present invention as compared with suturing by conventional techniques.

In Group 1, all twenty external ring technique arterial anastomoses were patent both at one week and at four to six weeks. However, three of the twenty conventional anastomoses were thrombosed at one week, and an additional seven were thrombosed at four to six weeks (FIG. 5). Even among the originally patent, in seventeen of the twenty conventional anastomoses, diminished flow during radical patency testing was observed as compared to flow through anastomoses effected with the external ring technique. This may have been a factor in the cases of later thrombosis. The difference bewteen the 50% late patency rate by the conventional technique and the 100% patency rate by the external ring technique was statistically significant (p 0.01).

In Group 2, all ten external ring technique arterial anastomoses were patent at six weeks. In contrast, at six weeks, three of the ten conventional anastomoses were thrombosed and two others demonstrated diminished flow during radical patency testing. The difference between the 70% patency rate by the conventional technique and the 100% rate by the external ring technique again was statistically significant (P 0.02). In neither group was there any occurrence of aneurysms, hematomas, or wound infections.

Figure 6:
FIG. 6 is electron micrograph of a rat's blood vessel which has been severed and rejoined by the method and apparatus of the present invention.

FIG. 6 is a scanning electron micrograph portraying one of the patent rat anastomosis performed by the external ring technique with normal intimal healing. It will be noted that slight tipping of the ring occurred; however, in no case did such tipping impede blood flow.

EXAMPLE II

Rat inferior epigastric veins (generally 0.7 mm. in diameter) were anastomosed end-to-side to femoral veins (generally 1.5 mm. in diameter) by conventional techniques in twenty control rats, using 6-8 sutures per anastomosis, and in an experimental group of twenty rats by the external ring technique using rings 0.2-0.3 mm. long of 16 gauge polytetrafluoroethylene with four notch pairs spaced 90° apart. The surgical technique was substantially identical to that used in Example I, except that the femoral veins were prepared for anastomosis by cutting 6 mm. openings in their side walls.

After five days, the control group had a 65% success rate whereas the experimental group exhibited 100% patency (P 0.01).

Figure 10:
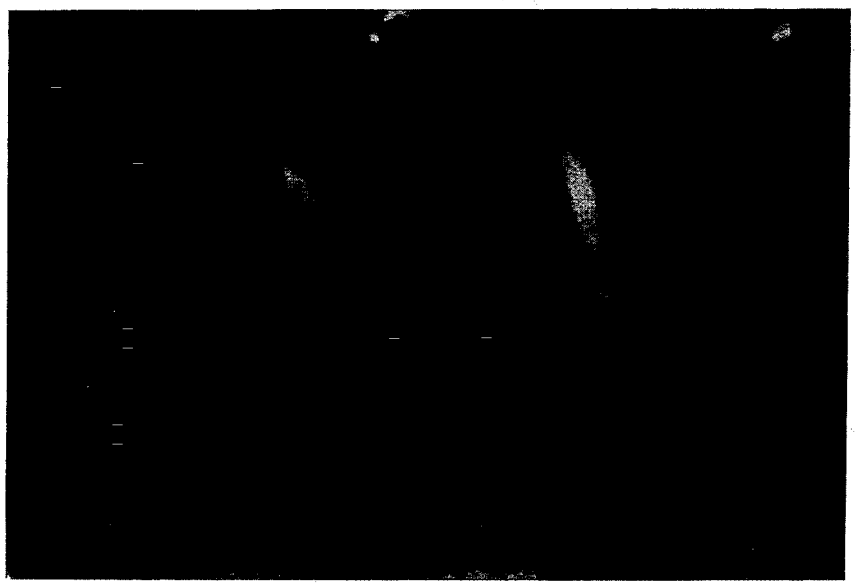
FIG. 10 is a photo micrograph of an end-to-side rat blood vessel anastomosis.

FIG. 10 is a photo micrograph portraying one of the patent rat end-to-side anastomosis performed by the external ring technique with normal intimal healing.

The external ring technique provides a direct approach to overcome the vessel's inherent circumferential compressive stress, provide maximal radial tethering forces at the site of anastomosis, and actually dilates the vessel at the very location platelet aggregation occurs in the early post-operative phase. These important factors explain the increased success rate in the difficult model of the 0.4 mm. size inferior epigastric artery of the rat. With any constant level of surgical skill, the success rate of microvascular repair falls as the vessel size decreases. Of course, the degree of skill acquired by the surgeon is an important factor in the success rate of microvasuclar repair, and the use of the external ring technique may actually improve any given level of surgical skill.

The external ring provided by the application is simply formed and easy to use. In surgery, where several anastomoses need be performed, the external ring technique will substantially reduce the time of the operation. The multidirectional radial tethering helps to assure dilation of the passageway at the interconnection, and interconnection with a large blood passageway is generally assured. The technique draws the intima of the severed ends in tight apposition to each other providing a fluid-tight interconnection and exposure of blood substantially entirely with the intima, reducing the chance of significant post operative thrombosis.

Encircling devices according to the invention are useful in joining or anastomosing other tubular anatomical structures. Illustrated in FIG. 20 is an anastomisis ring 500 which is used for an end-to-end anastomosis of a severed ureter 502. The ring, which is either absorbable or nonabsorbable, is placed over one end 502a of the ureter. The severed ureter ends are tethered to the ring with three or four evenly spaced sutures 504. One end of each suture 504 is slipped under the ring 500; the ring is positioned over the suture line; and the suture is tied over the ring with a surgeons knot 506. The tethering serves to enlarge the lumen opening 508 at the ureter ends and hold the ends together during healing. The anastomosis is leakproof and achieves proper mucosal alignment, helping to assure patency.

Illustrated in FIG. 21 is a ring 520 used for anastomosing ends of a fallopian tube 522 that were surgically severed to remove a short occluding section. The fallopian tube is supported between the uterus and the ovary by mesosalpinx tissue 524, and it is desirable, both for making the surgical procedure more comfortable and for maintaining the integrity of the fallopian tube-mesosalpinx bond, that the mesosalpinx not be severed at the junction of the tube ends. Accordingly, the ring 520 that is used in the end-to-end fallopian tube anastomosis is incomplete, having a small gap 526 allowing it to substantially surround the fallopian tube without extending through the mesosalpinx 524. The gap, however, is filled by the mesosalpinx, and hence, the gap does not significantly weaken the ring. The surgical procedure is similar to that used for joining blood vessel or ureter ends, and the anastomosis in which the fallopian tubes ends are tethered with sutures 527 to the ring provides mucosal allignment of the fallopian tube ends.

A particularly difficult surgical procedure is the repair of injured nerve, and an anastomosis ring 550 (FIG. 22) according to the invention can be used to repair a severed nerve 552 with a good possibility of functional recovery. In microsurgical practice, the primary objective of the surgeon is to repair the injured nerve with a technique that has the greatest probability of providing maximal functional recovery. The surgeon must choose among several of alternatives in the method repair; such as epineurial or fascicular repair, with sutures or sutureless, and the number of sutures; according to each clinical situation. There still exists an active controversy as to whether fascicular suture repair or epineurial suture repair gives the best functional recovery. It is also still unknown how various numbers of sutures affect functional recovery of the nerve. If the number of sutures is not enough, gaps are created at the outer epineurial sheath 556; however, if the number of sutures is too great, these sutures can occupy too much space in the nerve and cause excessive inflammation and scarring, creating barriers for axon regrowth. If the fasciculi 558 are improperly aligned, a large number of regenerating nonmyelinated axons can diverge off the longitudinal axis and escape through small gaps in the perineurium into the extrafascicular tissue and outside the endoneural tubes. These axons will be generally ineffectual in providing nerve recovery.

Through the use of the anastomosis ring 550, repair of the outer epineurial sheath 556 is effected without gaps being created and without the sutures occupying too much space in the nerve and impinging on the fasciculi 558. The ring 550 is placed around one end of the severed nerve 552 and sutures 560 are drawn through the apposed epineurial sheath ends 556 and tethered to the ring, holding the ends of the epineurial sheath 556 together with a minimal number, e.g., 3 to 4 sutures. As the sutures are tethered outward, they do not impinge on the fasciculi 558, thereby minimizing inflammation and scaring.

Furthermore, the outward radial tethering stress placed on the outer epinureal sheath 556 tends to hold the fasciculi 558 in axial alignment and in end-to-end apposition, resisting the tendency of the fasciculi ends to retract from each other. The fasciculi ends are brought together with a pressure that is not excessive, and the fasciculi brought together in this manner are neither folded excessively nor kinked.

An encircling device to which a tubular anatomical structure is tethered provides a simple means of surgically attaching the anatomical tubular structure to a body organ to communicate the tubular structure to an internal region or cavity of the organ. Ureteroneocystostomy, which is reattaching a ureter to the bladder, is the most frequently used anastomosis to restore the urinary tract. There must be neither tension nor redundant length of the ureter. To prevent obstruction at the ureteroneocystostomy, the tunnel through the bladder wall must be wide enough to allow free passage of the ureter. The most common technique is to incise the bladder wall longtiudinally, tunnel through the bladder wall, and suture the ureter to the bladder mucosa with an average of four sutures.

Illustrated in FIG. 23 is an absorbable ring 600 which is used for effecting a ureteroneocystostomy with a much less traumatic breach of the wall 601 of the bladder 602 (FIG. 24) and which avoids the need to suture the ureter 604 to the mucosa 603 of the bladder. Basically, the ring 600 is tethered to the end 606 of the ureter 604, holding its end open; a trocar 608 is driven obliquely through the wall of the bladder, and the ring that is connected to the ureter is inserted into the interior cavity 610 of the bladder. When the trocar 608 is withdrawn from the bladder, the bladder 601 constricts upon the passageway formed by penetration of the trocar, and the relatively large size of the ring 600 prevents it from being pulled from the bladder 602.

The absorbable ring 600 has a frustoconical configuration, having a narrower opening at an outer end 612 through which the ureter 604 is inserted and an opening at its inner end 614 with a diameter that is substantially greater than the exterior diameter of the ureter. The severed end of the ureter is inserted through the narrow end 612, and then sutures 616, e.g., four, are drawn through the end of the ureter and tied around the ring, tethering the end of the ureter to the ring 600 so that the end is held fully open with its lumen 618 preferably slightly enlarged as it is stretched toward the sidewall of the ring at its larger inner end 614.

Insertion of the ring-tethered end of the ureter 604 is illustrated in FIG. 24. The trocar 608 is inserted obliquely through the wall 601 of the bladder 602 providing a tunnel 620 of a size appropriate for passage of the ring 600. The trocar 608 is formed of flexible material and is longitudinally separable into two halves along splits 624, whereby it can be initially opened to surround the ureter, held together, e.g., with bands (not shown) and again separated to remove it from around the ureter after it has been withdrawn from the bladder 602. An insertion tool 626, shown in FIG. 26, is used to drive the ring-tethered end of the ureter 604 through the tunnel 624 provided by the trocar 608. The tool 626 is formed of flexible material and includes an open ring 628 at its lower end which is fitted around the ureter 604 and used to press against the outer surface of the ring 600 during insertion, an integrally formed elongated shaft 630 extending upward from the ring in an axial direction and having a length greater than the length of the trocar tunnel 620, and an integrally formed knob 632 at its upper end for gripping purposes. After the trocar penetrates the bladdar wall 601, the tool 626 is placed around the ureter and used to plunge the ring 600 into the trocar 608 beyond the mucosa 603 of the bladder. Then the tool 626 and trocar 608 are withdrawn, leaving the ring 600 within the bladder cavity 610.

After the trocar is withdrawn, the bladder wall 601 constricts around the ureter, preventing the relativity large ring 600 from removing itself through the insertion passageway through the bladder wall 601. Fluid pressure from the cavity 610 of the bladder 602 will push the ring into the mucosa 603 but not out from the bladder. To further assure that the ring does not remove itself from the bladder, the ring 600, preferably, has outwardly extending friction spikes 640 formed on its exterior surface to grip the mucosa as the ring is pushed thereagainst. After insertion of the ring-tethered ureter, the ureter 604 is secured to the exterior of the bladder with sutures 642 (FIG. 25).

The oblique insertion, i.e., at an angle of 45° or less relative to the outer wall of the ureter, provides a sufficient length of the ureter extending through the wall so that the natural constriction of the bladder wall 601 pinches the ureter 604, preventing back flow of fluid through the ureter. Peristaltic contractions of the bladder wall 601 conduct fluid from the kidney 644 into the bladder cavity 610.

Healing occurs along the exterior surface of the ureter with the bladder tissue along the passageway. The ring 600 holds the end of the ureter open during healing so that scar tissue does not close off the end of the ureter. By the time the ring is absorbed, there is no longer danger of scar tissue closing off the opening.

A new surgical technique similar to that described above for ureteroneocystostomy can be easily used for microsurgical uterotubal reconstruction in gynecology. This microsurgical technique simplifies the conventional technique and makes it more effective.

At present, microsurgical reconstruction of the obstructed uterine portion of the fallopian tube is designed to remove only the occluded area and then join the patent resected portions. In the conventional technique, the anastomosis is performed in two layers. The mucosal layer of the fallopian tube is sutured to the submucosal layers of the uterus using approximately four sutures. A water-tight closure of the mucosal layers is not necessary, but an accurate approximation of the mucosal surface is required. Approximately eight seromuscular sutures are then placed with the same suture material and technique.

The new technique does not require the use of a stent or prosthesis, and avoids the need to perform the difficult task of approximating and suturing the fallopian tube mucosal layer to the submucosal layer of the uterus. Instead, a frustoconical ring 700, similar to the ring 600 described above for ureteroneocystostomy, is used to locate the end of the fallopian tube 702 inside the uterus 704. The absorbable external ring 700 is placed on the end of the severed tube 702 by placing three or four sutures 710 through the muscular layer and then tethering the sutures over the ring. Tethering to the ring 700 forms a wider lumen of the fallopian tube and also anchors it inside the uterus. The trocar and tool, described above with respect to ureteroneocystostomy is used to place the ring-tethered tube inside of the uterus. Then six to eight seromuscular sutures 712 are attached to the tube and to the exterior of the uterus.

In the surgical procedure, the mucosa of the fallopian tube and uterus are not immediately brought together, and immediate healing occurs between the exterior of the uterus and the surrounding uterus walls, while the ring holds the end of the tube 702 open assuring patency. However, as the ring 700 is absorbed, the mucosa 706 of the uterus grows over the approximate end of the tube.

While the invention has been described in terms of certain preferred embodiments, modifications obvious to one with ordinary skill in the art may be made without departing from the scope of the invention. The embodiments of the encircling devices, described herein, are simple; however, modifications in device design will be made depending upon the material used and surgical considerations.

Various features of the invention are set forth in the following claims.

What is claimed is:

1. An encircling device formed of biocompatible material for joining a first tubular anatomical structure that is supported within the body by connective tissue and has a prepared open end, to a second anatomical structure, said device including a body which is substantially encircling an open interior region for receiving the end of the tubular anatomical structure, but which is not entirely encircling and has spaced ends closely adjacent with a gap therebetween, said gap being provided for accommodating the connective tissue supporting said first tubular anatomical structure, tethering means on the body at at least three spaced apart locations generally along a circle of substantially greater diameter than the diameter of the prepared open end for tethering the tubular anatomical structure thereto and for applying outward radial stress to the tubular anatomical structure, and means associated with the body for attaching said tethered tubular anatomical member to the second anatomical structure, said body being sufficiently rigid to act as the sole support for said anastomosed anatomical structures.

2. An encircling device formed of biocompatible material for microvascular anastomosis of a tubular anatomical structure having a prepared end opening and a second anatomical structure having a prepared opening, said encircling device including a body having an open interior region for receiving the end of said tubular anatomical structure, hook means at least three spaced apart locations on said body generally along a circle of substantially greater diameter than the diameter of the tubular anatomical structure for penetrating the walls of both anatomical structures, tethering the anatomical structures thereto along their prepared openings and for applying outward radial stress to the anatomical structures, dialating and apposing the same to form a substantially fluid-tight peripheral seal along the prepared openings, said body being formed at least in part of flexible, resilient material, whereby said body is deformable out of plane to facilitate penetration of the walls with said hook means, and thereafter returns to its nondeformed state, and said body in its nondeformed state having sufficient rigidity to provide the sole support for said anastomosed structures during healing.

3. A device according to claim 2 in which the body is formed of a material that is dissolved or degraded in the body after a period of time.

4. A device according to claim 2 in combination with a clamping device comprising a base, means extending from said base at spaced apart locations for clamping the anatomical structures to hold them in close proximity for anastomosis, and means connecting said encircling device to said base, said connecting means holding said device in axial alignment with the tubular anatomical structure held by one of said clamping means.

5. A combination in accordance with claim 4, said clamping means including a fluid pressurized bladder, means for supplying pressurized fluid to said bladder and means for adjusting the fluid pressure supplied to said bladder to vary the gripping force of said clamping means on the anatomical structures.

6. A method of joining a first tubular anatomical structure having a prepared open end to a second anatomical structure having a wall defining a cavity, the method comprising
providing an encircling device having a body that defines an interior opening,
extending said tubular anatomical structure through said interior opening and tethering said prepared open end to said body to insure that said end is held open,
inserting a trocar through the wall of said second anatomical structure and into the cavity to provide a tunnel into the cavity,
driving said encircling device and said tethered tubular anatomical structure into said tunnel to locate said encircling device interior of the cavity, and
withdrawing said trocar leaving said encircling device within the cavity and said tubular anatomical structure extending through the wall and into the cavity with its end held open within the cavity.

7. A method according to claim 6 including suturing said tubular anatomical structure to the exterior of said second anatomical structure after withdrawal of the trocar.

8. A method according to claim 6 including providing a driving tool having an open ring for substantially encircling said tubular anatomical structure and a shaft extending in an axial direction from said ring having a length greater than the length of said tunnel, and driving said substantially encircling member through said trocar with said tool.

9. A method of anastomosing a first blood vessel having a prepared open end to the side of a second blood vessel which is atherosclerotic having a plaque formed along its interior surface, the method comprising,
providing an encircling device having a body defining an open interior region for receiving the prepared end of the first blood vessel,
tethering the prepared end of the first blood vessel to said body at at least three locations generally along a circle of substantially greater diameter than the diameter of the prepared open end, applying radial outward stress to the prepared end of the first blood vessel,
coring an opening in the side of said second blood vessel to provide an opening portion through the wall of said second blood vessel matched in diameter to the exterior diameter of said encircling device and an opening portion through the plaque of lesser diameter, leaving an annulus of said plaque,
inserting said device, to which the first blood vessel is sutured, into said larger diameter opening portion, and
securing said device within said larger diameter opening portion.

10. A method according to claim 9 wherein said device is secured within said larger diameter opening portion by wrapping said blood vessel portions with a biocompatible adhesive tape.

11. An encircling device formed of biocompatible material for joining a tubular anatomical structure having a prepared opening to a second anatomical structure having a wall defining a cavity, said device having a body in the shape of frustoconical ring defining an open interior for receiving the tubular anatomical structure therethrough, said open interior having an outer opening that is generally matched in diameter to the diameter of the tubular anatomical structure and having an inner opening that is of substantially larger diameter, and tethering means at least three spaced apart locations on the body generally along a circle of substantially greater diameter than the diameter of the prepared end opening for tethering the tubular anatomical structure thereto, said tethering means providing for applying outward radial stress to the tubular anatomical structure to hold open the prepared opening, the frustoconical structure having the enlarged end acting as means for preventing removal of the device body when inserted into the cavity with the tethered tubular structure extending through the wall of said second anatomical structure.

12. A device in accordance with claim 11, wherein outwardly extending friction spikes are disposed on the exterior surface of said frustoconical body to further prevent removal of said device body.

13. A unitary encircling device formed of biocompatible material for joining a tubular anatomical structure having a prepared opening to a second anatomical structure having a wall defining a cavity, said device having a body defining an interior opening for receiving the tubular anatomical structure, tethering means at at least three spaced apart locations on the body generally along a circle of substantially greater diameter than the diameter of the prepared end opening for tethering the tubular anatomical structure thereto, said tethering means providing for applying outward radial stress to the tubular anatomical structure to hold open the prepared opening, friction spikes disposed on the exterior surface of said body for engaging the wall of said second anatomical structure for preventing removal of said body when inserted into the cavity with the tethered tubular structure extending through the wall of the second anatomical structure, said body being in the shape of a frustoconical ring having an outer opening generally matched in diameter to the diameter of the tubular anatomical structure and having a substantially larger diameter inner opening.

* * * * *